United States Patent [19]

Wong et al.

[11] Patent Number: 4,777,139

[45] Date of Patent: Oct. 11, 1988

[54] HEMATOLOGY CONTROL OR CALIBRATOR WITH RED CELL COMPONENTS OF ENHANCED STABILITY

[75] Inventors: Show-Chu Wong, West Nyack; Harbans S. Deol, Walden; Debra L. Harz, Spring Valley; Jill H. Davidson, Monsey, all of N.Y.

[73] Assignee: Fisher Scientific Company, Pittsburgh, Pa.

[21] Appl. No.: 66,265

[22] Filed: Jun. 25, 1987

[51] Int. Cl.$^4$ ............................................. G01N 31/00
[52] U.S. Cl. ........................................ 436/18; 436/10; 436/17; 252/408.1
[58] Field of Search ........................................ 436/8–18; 424/3; 422/61, 73; 252/408.1

[56] References Cited

U.S. PATENT DOCUMENTS

| | | | |
|---|---|---|---|
| 3,708,572 | 1/1973 | Peetoom et al. | 436/10 |
| 3,973,913 | 8/1976 | Louderback | 436/10 |
| 4,107,287 | 8/1978 | Morton et al. | 424/3 |
| 4,324,687 | 4/1982 | Louderback et al. | 436/10 |
| 4,358,394 | 11/1982 | Crews et al. | 252/408.1 |
| 4,390,632 | 6/1983 | Carter | 436/10 |
| 4,489,162 | 12/1984 | Hawkins et al. | 436/10 |
| 4,579,824 | 4/1986 | Louderback et al. | 436/10 |
| 4,698,312 | 10/1987 | Wong et al. | 436/10 |

OTHER PUBLICATIONS

Philip I. Smith et al, "Acrolein/Glutaraldehyde as a Fixative for Combined Light and . . . ", J. Histochem & Cytochem, 30(12), pp. 1307–1310 (1982).
M. A. Hayat, Principles and Techniques of Electron Microscopy, vol. 1, pp. 65–107 (1970).
T. Saito et al, "Acrolein as a Fixative for Enzyme Cytochemistry", J. Histochem & Cytochem, vol. 24, No. 12, pp. 1258–1269 (1976).

*Primary Examiner*—Barry S. Richman
*Assistant Examiner*—T. J. Wallen
*Attorney, Agent, or Firm*—Alan M. Doernberg

[57] ABSTRACT

Red cells are exposed to an unsaturated aldehyde such as acrolein (propenal) under conditions sufficient to increase the stability of the cells without impairing the ability of a lysing reagent to lyse the cells. After treatment, the treated cells are washed and are suspended in a stabilizing suspension medium.

10 Claims, No Drawings

HEMATOLOGY CONTROL OR CALIBRATOR WITH RED CELL COMPONENTS OF ENHANCED STABILITY

The present invention relates to hematology controls and calibrators, and especially to the lysable red cell component of such controls or calibrators.

Controls or calibrators for hematology instruments are suspensions in isotonic medium of a cellular component that mimics a patient's red cells, a cellular (or synthetic) component that mimics a patient's white cells and, frequently, a cellular component that mimics a patient's platelets. Unlike the white cell component, the red cell components should be lysable by the lysing reagent (typically one or more quaternary ammonium salts). In the red cell channel of the instrument, the red cell component should act like normal red cells and yield reproducible values of such parameters as mean cell volume (MCV), total cell count, hemoglobin, RDW and hematocrit. Once the red cell component is lysed (and converted by cyanide to cyanohemoglobin), a reproducible hemoglobin value should be obtained (from which the instrument can calculate hematocrit and other derived parameters.

The limited shelf life of hematology controls and calibrators is normally due to the red cell component changing over time in one of the measured parameters: either hemolyse in isotonic medium to change the cell count or swelling or shrinking in the isotonic medium to change MCV, hematocrit and RDW values.

Various attempts have been made to stabilize the red cell component either by pretreatments prior to suspending in the isotonic medium or by incorporating additives in the isotonic medium (osmotically balanced). For example, U.S. Pat. No. 4,358,394 to Crews, et al (1982) discloses red cells treated in a multicomponent preconditioning diluent (containing, e.g., lactose and a non-ionic surfactant) and then separating the red cells and adding them to an isotonic medium containing lactose, bactericides and fungicides, albumen and a bile salt, cholic acid derivative or phenothiazine. See also, U.S. Pat. No. 4,299,726 to Crews, et al (1981). U.S. Pat. No. 3,873,467 to Hunt (1975) discloses washing, swelling and fixing the cells with a multicomponent fluid (which may include a small amount of aldehyde to toughen the cell membranes, col. 2, lines 47-49) and then suspending the cells in a suspension fluid. The treated cells are still lysable when later exposed to lysing reagent. The washing fluid indicated as typical contained 0-0.00008 molar glutaraldehyde. Other uses of aldehydes are disclosed, e.g., in U.S. Pat. No. 4,390,632 to Carter (1983), and in copending, commonly-assigned U.S. Ser. No. 889,748 of Wong, et al, filed July 28, 1986, now U.S. Pat. No. 4,698,312.

U.S. Pat. No. 4,579,024 to Louderback, et al discloses red cells treated with aldehyde (e.g., 40 ml of 37% formaldehyde and 500 ml of 0.9% saline) for two hours at 18°-28° C. whereby they retain their plasticity for up to about 5 days. Then, before the cells have become rigid, they are retained in Alsevier's Solution with about 0.01% to 0.21% NaCl to provide an osmotic pressure to yield a desired cell size (MCV). Formaldehyde and glutaraldehyde on the aldehydes disclosed. Sucrose is disclosed for use in the modified Alsevier's Solution for certain levels.

U.S. Pat. No. 4,489,162 to Hawkins, et al (1984) discloses hematology controls and calibrators wherein the suspending medium contains 5-50 grams per liter of a disaccharide such as lactose or sucrose.

In a field unrelated to hematology controls and calibrators, it is known that aldehydes such as formaldehyde, acetaldehyde and glutaraldehyde are commonly used in fixing tissue for microscopic examination. The unsaturated aldehyde acrolein (or propenal) has also been used for fixing tissue, especially for electron microscopic examination. For such tissue fixation, acrolein is reported to rapidly stabilize cells or tissue with minimal morphological change.

BRIEF DESCRIPTION OF THE INVENTION

Unsaturated aldehydes such as acrolein (propenal) have been found efficacious in the stabilization of erythrocytes (human, particularly) for use as the lysable red cell component of hematology controls and calibrators. Accordingly, the present invention provides a hematology control or calibrator comprising a suspension of treated erythrocytes in a stabilizing medium, characterized by the treated erythrocytes having been exposed to a aliphatic unsaturated aldehyde of 3-6 carbons under conditions sufficient to increase the stability of the treated erythrocytes in the medium without impairing the ability of a lysing reagent to lyse the treated erythrocytes in a hematology analyzer.

The present invention further provides a process for preparing a hematology control or calibrator comprising the steps:

(a) Exposing washed erythrocytes to an unsaturated aldehyde at a treatment concentration and temperature for a treatment time period, (b) After the treatment time period, washing the treated erythrocytes, and (c) Suspending the treated and washed erythrocytes in a stabilizing suspending medium, the treatment concentration, temperature and time being sufficient to increase the stability of the treated erythrocytes in suspending medium without impairing the ability of a lysing reagent to lyse the treated erythrocytes in a hematology analyzer.

DETAILED DESCRIPTION OF THE INVENTION

In the present invention, red cells are stabilized by treatment with an unsaturated aldehyde under controlled conditions. The conditions (especially aldehyde concentration, time and temperature) are not individually critical but are rather selected together, as described and illustrated below, to yield a result of improved stability (particularly of MCV values) without detracting from ability to lyse the cells in the white cell channel of a hematology instrument.

The red cells used can be human (fresh or expired) or from various mammalian sources (e.g., bovine). The red cells are normally washed to remove contaminants and endogenous white cells and platelets (the buffy coat) before treatment; however, final removal of remaining white cells (such as by filtration through a filter to which white cells, and especially granulocytes adhere), if employed, can either precede or follow treatment with aldehyde.

The aldehyde can be propenal (acrolein) or another aliphatic unsaturated aldehyde of 3-6 carbons such as 2-butenal, 3-butenal, 2-hexenal, 4-methyl-2-pentenal or other similar compounds. Such aldehyde can be of varying concentration in the liquid phase at the time of treatment; representative concentration is in the range of 0.01% to 1.0%. By comparison, the formaldehyde concentration in U.S. Pat. No. 4,579,824 is 37% diluted 40/540 or 2.7%. It should be apparent that propenal can be used herein at concentrations lower than proposed for formaldehyde in certain prior art.

The treatment temperature can be from about 0° C. to about 30° C., and even higher if treatment time is controlled very carefully. Room temperature conditions (e.g., 20°–25° C.) can be employed with careful control of temperature and time. Thus, if 150 minutes at 24° C. is chosen, essentially identical results will be obtained even if temperature varies one degree or time varies 15 minutes. Wider variations will yield controls or calibrators with suitable properties; those properties may, however, depart from the expected values one would obtain if the design conditions are maintained. Refrigeration conditions, such as 0°–5° C. (e.g., 4° C.) can be employed with more latitude on treatment time and temperature. This enables better control during large scale processing. Thus, properties are not expected to vary appreciably whether treatment at 4° C. proceeds for 15, 20 or 25 hours or whether refrigeration temperatures vary from 2° C. to 5° C. Freezing temperatures should be avoided.

At the conclusion of the treatment by unsaturated aldehyde, the red cells are separated from the aldehyde solution and washed in normal saline or osmotically-controlled medium. The treated cells can then be suspended in the desired final stabilizing media. The process of this invention can be employed with fresh blood cells (i.e., within 5 days), aged red blood cells and/or expired red blood cells for use in a whole blood controls/calibrators. Formulations of stabilizing media for conferring long-term stability on hematology controls and calibrators are given below:

| Distilled Water | 800 ml |
| Sodium Citrate, dihydrate | 3.20–6.32 gm |
| Citric Acid | 0.22–0.43 gm |
| Sodium Chloride | 1.68–3.32 gm |
| Adenine Sulfate | 0.08–0.16 gm |
| Sodium Salt of Nalidixic Acid | 0.064–0.126 gm |
| Sodium Omadine (Sod. Pyrithione) | 0.003–0.006 gm |
| Chloramphenicol | 0.040–0.080 gm |
| Ampicillin | 0.064–0.126 gm |
| Amikacin | 0.064–0.126 gm |
| Gentamicin Sulfate | 0.064–0.126 gm |
| Bovine Albumin (30%) | 20.0–39.5 ml. |
| q.s. to 1 liter with distilled water | |

For the best results, the above ingredients are added to distilled water in the order listed in the table, allowing each ingredient to dissolve completely before the following ingredient is added. The solution then filtered through 0.2μ filter and used for resuspending washed red blood cells and/or formulation. Different levels are achieved by initially selecting small, medium or large cells and by adding different concentrations of such cells to media of different specific formulation with the above ranges.

Upon suspension in such media, the cells will normally shrink or swell to an equilibration value of MCV. Thus, for example, cells with an MCV of 77.8 before treatment and 74.7 after treatment (with 0.1% acrolein) have been found to stabilize in the above suspending medium for Level I. Similar stability was achieved with red cells having an MCV before treatment of 82.1 and after treatment of 80.0 (used for Level II) and with red cells having an MCV before treatment of 90.0 and after treatment of 90.2 (used for Level III). Equilibrations took approximately 35, 25 and 10 days for Levels I, II and III, respectively. Once, however, the MCV values stopped changing, they remained constant (within tolerances of 1 MCV unit) for 90 days or longer. These equilibrations are of a different type than the five day or less equilibrations of U.S. Pat. No. 4,579,824 used to enable a single pool of cells to be employed for all three

EXAMPLE 1

Packed red blood cells were separated from a CPD-A whole blood by conventional blood bank techniques to remove platelet rich plasma and buffy coat (white cell concentrated layer), washed (each unit individually) with 30 mm citrate-saline, pH 6.0, and expressed buffy coat by conventional aseptic techniques. To the washed packed cells (in a plastic bag) were added equal volume of 0.2% acrolein in 6.5 mm phosphate-saline, pH 7.2 (PBS). The suspended cells were kept at 4° C. overnight (16–19 hours), then washed with PBS twice by conventional centrifugation method and, at the time, expressed to remove buffy coat material if needed. The washed/stablilized cells were filtered through leukofilter (polyester filter) and were ready to formulate with white cells and platelet components into appropriate levels of control or calibrator in suspending medium. The real-time, open vial and other stabilities of the control, or calibrator were analyzed on a Coulter S+IV hematology analyser. The major problem/drawback of a long-stability product is usually the real-time stability if the MCV of the red cell component in hematology control or calibrator. Therefore, the improved stability of MCV is the most significant index for improvement. The real-time/long term stability results of MCV from various levels formulation as shown in Table1.

TABLE 1

| | (0.1% Acrolein) | | |
| | | MCV | |
| Days | Low | Normal | High |
| --- | --- | --- | --- |
| 1 | 77.8 | 82.1 | 90 |
| 2 | 77.3 | 82 | 89.7 |
| 8 | 76.5 | 80.5 | 89.6 |
| 11 | 76.3 | 80.5 | 89.6 |
| 15 | 76 | 80.8 | 90.2 |
| 21 | 75.8 | 80.7 | 90.5 |
| 25 | 75.1 | 80.1 | 90.1 |
| 39 | 75.2 | 80 | 90.5 |
| 49 | 74.8 | 79.6 | 90.2 |
| 56 | 74.8 | 79.7 | 90.2 |
| 66 | 74.6 | 79.5 | 89.8 |
| 78 | 73.8 | 78.8 | 89.4 |
| 87 | 74.4 | 79.4 | 89.9 |
| 98 | 74.5 | 79.7 | 90.3 |
| 107 | 74.3 | 79.5 | 90 |
| 119 | 74.1 | 79.4 | 89.6 |
| 128 | 74.8 | 79.7 | 90.2 |
| 137 | 74.2 | 79.2 | 89.5 |
| 163 | 74 | 79.1 | 89.6 |
| 176 | 74.2 | 79.2 | 89.6 |
| 190 | 74.7 | 79.4 | 89.9 |

EXAMPLE 2

The buffy coat removed packed red blood cells were washed with the citrate-saline twice by conventional techniques as in Example 1.Buffy coat residue was processed in the bag. The washed cells were filtered through leuko-filter and collected in an appropriate sterile container and an equal volume of 0.1% acrolein in PBS added. The well suspended cells were kept at room temperature (ambient temperature) for 2½ hours, and then 1/20 volume of 1 M glycerine in PBS was added to neutralize excess aldehyde for 10-20 minutes. The suspension was then centrifuged to remove supernatant, then washed with PBS buffer twice and then used for pilot formulation as in Example 1. The real-time stability of MCV was measured over time, with the results shown in Table 2.

TABLE 2

| | (0.05% Acrolein) | | |
|---|---|---|---|
| | | MCV | |
| Days | Low | Normal | High |
| 0 | 94.4 | 94.2 | 94.6 |
| 5 | 92.9 | 93.1 | 93.8 |
| 15 | 90.8 | 92 | 94.5 |
| 26 | 90.1 | 92.2 | 95.9 |
| 40 | 89.3 | 91.9 | 97.1 |
| 57 | 86.5 | 89.8 | 95.5 |
| 77 | 87.8 | 91.2 | 98.2 |
| 96 | 87.2 | 90.9 | 97.9 |
| 106 | 87.3 | 90.6 | 97.6 |
| 130 | 87.5 | 90.7 | 98 |
| 173 | 87.6 | 90.8 | 98.6 |
| 188 | 86.8 | 90.7 | 98.4 |
| 189 | 87 | 90.8 | 97.8 |
| 190 | 87 | 90.6 | 97.2 |
| 195 | 87.7 | 90.5 | 97.7 |
| 209 | 87.5 | 90.5 | 97.6 |
| 226 | 87.5 | 90.7 | 97 |

What is claimed is:

1. A hematology control or calibrator comprising a suspension of treated erythrocytes in a stabilizing medium, characterized by the treated erythrocytes having been exposed to a aliphatic unsaturated aldehyde of 3-6 carbons under conditions sufficient to increase the stability of the treated erythrocytes in the stabilizing medium without impairing the ability of a lysing reagent to lyse the treated erythrocytes in a hematology analyzer.

2. The hematology control or calibrator of claim 1 wherein the aliphatic unsaturated aldehyde is propenal.

3. The hematology control or calibrator of claim 2 wherein the treated erythrocytes have been exposed to propenal at a concentration of about 0.01% to about 1.0% for a time of about 5 minutes to about 24 hours at a temperature from about 0° C. to about 30° C.

4. The hematology control or calibrator of claim 3 wherein the temperature is about 20°-25° C., the time is about 1 to 4 hours and the concentration is about 0.02-0.2%.

5. The hematology control or calibrator of claim 3 wherein the temperature is about 0°-5° C., the time is about 15-30 hours and the concentration is about 0.02-0.2%.

6. A process for preparing a hematology control or calibrator comprising the steps:
 (a) exposing washed erythrocytes to an unsaturated aldehyde at a treatment concentration and temperature for a treatment time period,
 (b) after the treatment time period, washing the treated erythrocytes, and
 (c) suspending the treated and washed erythrocytes in a stabilizing suspending medium the treatment concentration, temperature and time being sufficient to increase the stability of the treated erythrocytes in suspending medium without impairing the ability of a lysing reagent to lyse the treated erythrocytes in a hematology analyzer.

7. The process of claim 6 wherein the aliphatic unsaturated aldehyde is propenal.

8. The process of claim 7 wherein the treatment concentration is about 0.01% to about 0.5%, the treatment temperature is about 0° C. to about 30° C. and the treatment time is about 5 minutes to about 24 hours.

9. The process of claim 8 wherein the treatment concentration is about 0.02 to about 0.2%, the treatment temperature is about 20° C. to about 25° C. and the treatment time is about 1 to 4 hours.

10. The process of claim 8 wherein the treatment concentration is about 0.02% to about 0.2%, the treatment temperature is about 0° C. to about 5° C. and the treatment time is about 15-30 hours.

* * * * *